US012589038B2

(12) United States Patent
Koga et al.

(10) Patent No.: US 12,589,038 B2
(45) Date of Patent: Mar. 31, 2026

(54) MOBILE DIAGNOSIS SYSTEM AND TRANSPORT MANAGEMENT DEVICE

(71) Applicant: CANON MEDICAL SYSTEMS CORPORATION, Otawara (JP)

(72) Inventors: Akihiro Koga, Shinagawa (JP); Keisuke Hashimoto, Nasushiobara (JP); Katsuhiko Fujimoto, Saitama (JP); Fuminori Fujita, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 333 days.

(21) Appl. No.: 18/324,256

(22) Filed: May 26, 2023

(65) Prior Publication Data

US 2023/0381038 A1 Nov. 30, 2023

(30) Foreign Application Priority Data

May 30, 2022 (JP) ................................. 2022-087661

(51) Int. Cl.
*A61G 3/00* (2006.01)
*G16H 40/40* (2018.01)
(52) U.S. Cl.
CPC ............. *A61G 3/001* (2013.01); *G16H 40/40* (2018.01)

(58) Field of Classification Search
CPC ...................................................... A61G 3/001
See application file for complete search history.

(56) References Cited

U.S. PATENT DOCUMENTS

| | | | | |
|---|---|---|---|---|
| 5,775,758 A | * | 7/1998 | Eberspacher | ............. B60P 3/14 |
| | | | | 296/19 |
| 11,083,649 B1 | * | 8/2021 | Allen | ......................... B60P 3/34 |
| 2022/0359068 A1 | * | 11/2022 | Abdulkarim | ........... G16H 10/40 |
| 2024/0358565 A1 | * | 10/2024 | Joudrie | ................... A61G 3/001 |
| 2025/0213403 A1 | * | 7/2025 | Chandra | ................ A61G 1/044 |

FOREIGN PATENT DOCUMENTS

| | | | | |
|---|---|---|---|---|
| CN | 106184419 A | * | 12/2016 | ............. B62D 31/04 |
| GB | 2477799 A | * | 8/2011 | ................ B60P 3/14 |
| JP | 2017-12577 A | | 1/2017 | |

* cited by examiner

*Primary Examiner* — Faye M Fleming
(74) *Attorney, Agent, or Firm* — Oblon, McClelland, Maier & Neustadt, L.L.P.

(57) ABSTRACT

A mobile diagnosis system according to an embodiment includes a plurality of containers and a mobile body. The plurality of containers store medical equipment and can be combined with each other. The mobile body is configured such that a combination of the containers suitable for a person or a region requiring a medical service among the plurality of containers is loaded thereon, and transports the containers to the person or the region.

10 Claims, 6 Drawing Sheets

MOBILE DIAGNOSIS SYSTEM AND TRANSPORT MANAGEMENT DEVICE

CROSS-REFERENCE TO RELATED APPLICATION

The present application claims priority based on Japanese Patent Application No. 2022-087661, filed May 30, 2023, the content of which is incorporated herein by reference.

FIELD

The present specification and embodiments disclosed in the drawings relate to a mobile diagnosis system and a transport management device.

BACKGROUND

Due to an uneven distribution of doctors, aging of doctors, lack of social infrastructure, and the like, there are people and regions that cannot receive appropriate medical services when they need them.

DETAILED DESCRIPTION

Hereinafter, a mobile diagnosis system and a transport management device according to embodiments will be described with reference to the drawings. The mobile diagnosis system according to the embodiment includes a plurality of containers and a mobile body. The plurality of containers accommodate medical equipment and can be combined with each other. The mobile body has the containers loaded thereon and transports the containers to a person or a region requiring medical services, the containers being combined to be suitable for the person or the region among the plurality of containers.

First Embodiment

[Configuration of Mobile Diagnosis System]

Figure 1:
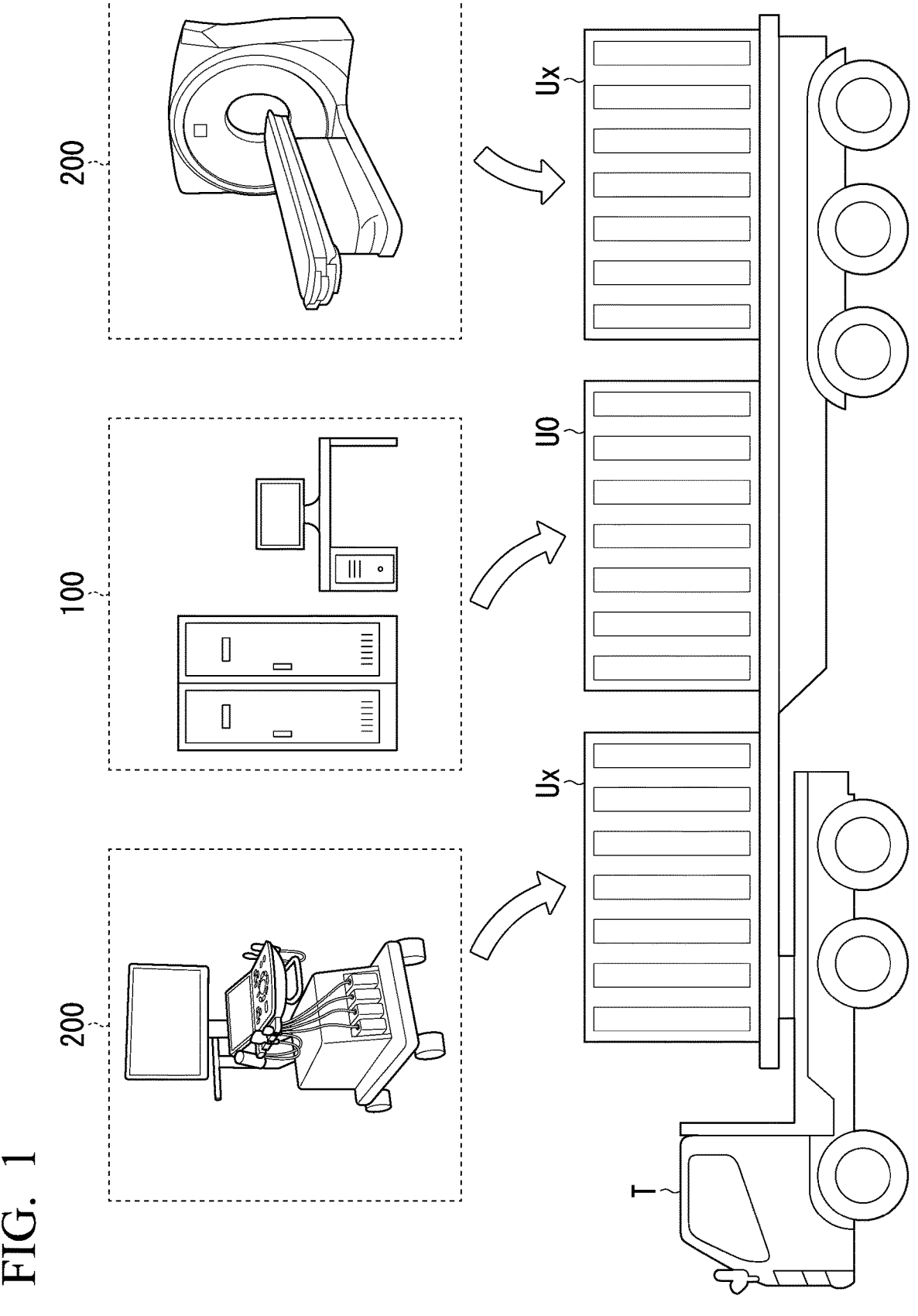
FIG. 1 is a diagram illustrating a configuration example of a mobile diagnosis system in a first embodiment.

FIG. 1 is a diagram illustrating a configuration example of a mobile diagnosis system 1 according to a first embodiment. The mobile diagnosis system 1 includes a plurality of containers and a mobile body T on which the plurality of containers are loaded. The plurality of containers include a container in which a transport management device 100 is stored (hereinafter referred to as a basic unit U0) and a container in which medical equipment (modality) 200 is stored (hereinafter referred to as a medical treatment unit Ux).

The medical equipment 200 is, for example, an X-ray computed tomography (CT) device, a magnetic resonance imaging (MRI) device, a sound wave image diagnosis device, or the like. The medical equipment 200 is typically placed on the floor of the container, but is not limited thereto. The medical equipment 200 may be installed on the wall, ceiling, or the like of the container.

A person can enter each container (unit). For example, the basic unit U0 not only stores the transport management device 100 but also has a space where people can change their clothes, and lockers for storing clothes and luggage, and the like are installed therein.

The mobile body T is typically a trailer truck, but is not limited thereto. For example, the mobile body T may be other means of transportation such as an aircraft, a ship, or a railroad vehicle. Description will be given below on the assumption that the mobile body T is a trailer truck as an example. The trailer truck T has the basic unit U0 and the medical treatment unit Ux loaded thereon, and transports the loaded unit to people or regions that cannot receive appropriate medical services when they need them due to various circumstances. The various circumstances include, for example, an uneven distribution of doctors, aging of doctors, lack of social infrastructure, and the like. Hereinafter, people to whom each unit is transported (that is, people who cannot receive appropriate medical services when they need them) will be described as "target patients" and regions to which each unit is transported (that is, regions that cannot receive appropriate medical services when they need them) as "target regions."

[Configuration of Transport Management Device]

Figure 2:
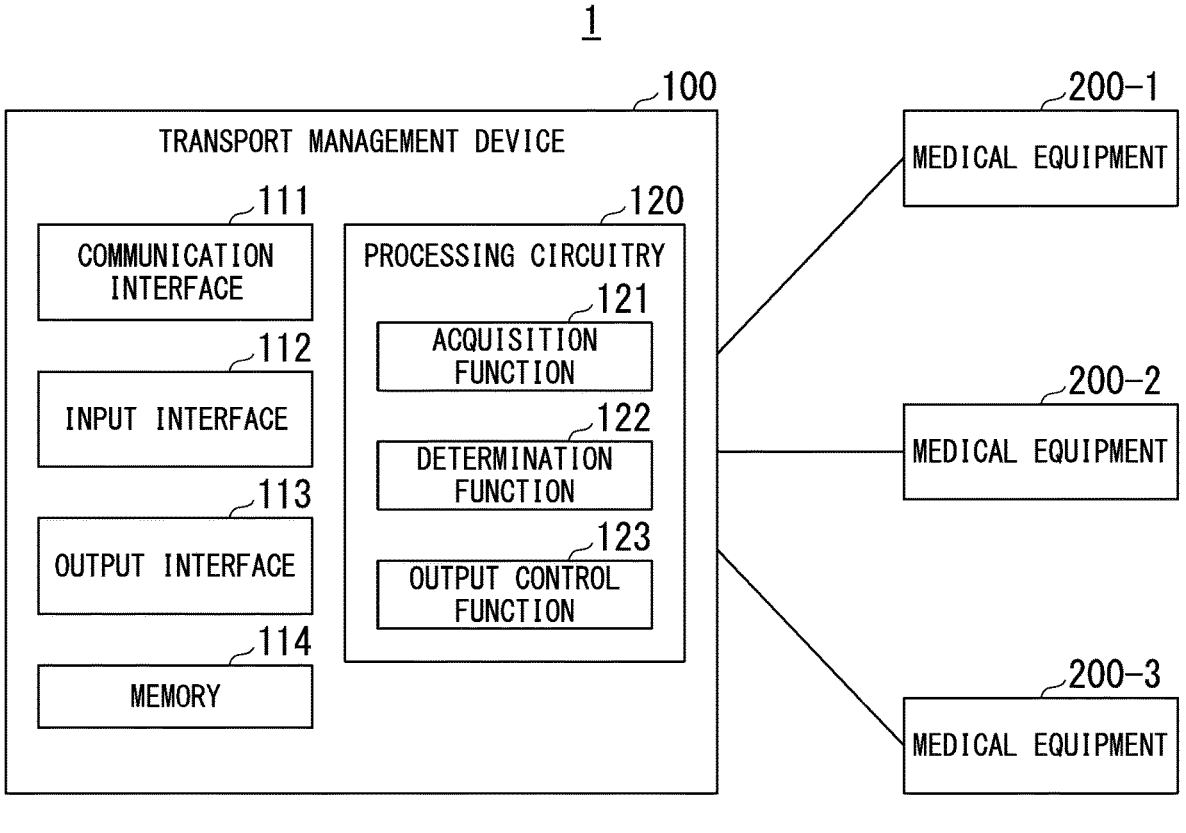
FIG. 2 is a diagram illustrating a configuration example of a transport management device in the first embodiment.

FIG. 2 is a diagram illustrating a configuration example of the transport management device 100 according to the first embodiment. The transport management device 100 includes, for example, a communication interface 111, an input interface 112, an output interface 113, a memory 114, and a processing circuitry 120.

The communication interface 111 communicates with external devices via a communication network NW. The communication network NW includes a local area network (LAN) and a wide area network (WAN). The external devices include the medical equipment 200 (200-1 to 200-3 in the example illustrated in the drawing) stored in the respective medical treatment units Ux, and the like. The communication interface 111 includes, for example, a network interface card (NIC), an antenna for wireless communication, a connector that can be connected to the medical equipment 200 in the medical treatment unit Ux in a wired or wireless manner, and the like.

The input interface 112 receives various input operations from an operator, converts the received input operations into electrical signals, and outputs the electrical signals to the processing circuitry 120. For example, the input interface 112 includes a mouse, a keyboard, a trackball, a switch, a button, a joystick, a touch panel, and the like. The input interface 112 may be, for example, a user interface that receives a sound input such as a microphone. When the input interface 112 is a touch panel, the input interface 112 may also have a display function of a display 113a included in the output interface 113 to be described later.

Note that the input interface 112 in this specification is not limited to one equipped with physical operation parts such as a mouse and a keyboard. Examples of the input interface 112 also include an electrical signal processing circuitry that receives an electrical signal corresponding to an input operation from external input equipment provided separately from the device and outputs the electrical signal to a control circuit.

The output interface 113 includes, for example, the display 113a, a speaker 113b, and the like. The display 113a displays various information. For example, the display 113a displays an image generated by the processing circuitry 120, a graphical user interface (GUI) for receiving various input operations from an operator, and the like. For example, the display 113a is a liquid crystal display (LCD), an organic electro luminescence (EL) display, or the like. The speaker 113b outputs information input from the processing circuitry 120 as a sound.

The memory 114 is implemented by, for example, semiconductor memory elements such as a random access memory (RAM) and a flash memory, a hard disk, and an optical disc. These non-transitory storage media may be implemented by other storage devices connected via a communication network NW such as a network attached storage (NAS) and an external storage server. In addition, the memory 114 may include non-transitory storage media such as a read only memory (ROM) and a register.

The memory 114 stores various processing results obtained by the processing circuitry 120 in addition to programs or instructions executed by a hardware processor. In addition, the memory 114 may store electronic medical records of a target patient and a person in a target region. The electronic medical records include, for example, medical interview results, medical treatment results, and information on the course of a patient's medical treatment such as a medical history.

The processing circuitry 120 has, for example, an acquisition function 121, a determination function 122, and an output control function 123. The processing circuitry 120 implements these functions, for example, by causing a hardware processor (computer) to execute programs or instructions stored in the memory 114 (storage circuitry). The processing circuitry 120 is an example of a "processing unit."

The hardware processor in the processing circuitry 120 is, for example, a circuitry such as a central processing unit (CPU), a graphics processing unit (GPU), an application specific integrated circuit (ASIC), a programmable logic device (for example, a simple programmable logic device (SPLD) or a complex programmable logic device (CPLD), or a field programmable gate array (FPGA)). Instead of storing the programs in the memory 114, the programs may be configured to be incorporated directly into the circuitry of the hardware processor. In this case, the hardware processor implements the functions by reading and executing the programs embedded in the circuitry. The above-mentioned programs may be stored in the memory 114 in advance, or may be stored in a non-temporary storage medium such as a DVD or a CD-ROM and installed in the memory 114 from the non-temporary storage medium by the non-temporary storage medium being mounted on a drive device (not illustrated) of the user interface 10. The hardware processor is not limited to being a single circuit, and may be one hardware processor by combining a plurality of independent circuits to implement the functions. In addition, a plurality of components may be integrated into one hardware processor to implement the functions.

[Processing Flow of Mobile Diagnosis System]

Figure 3:
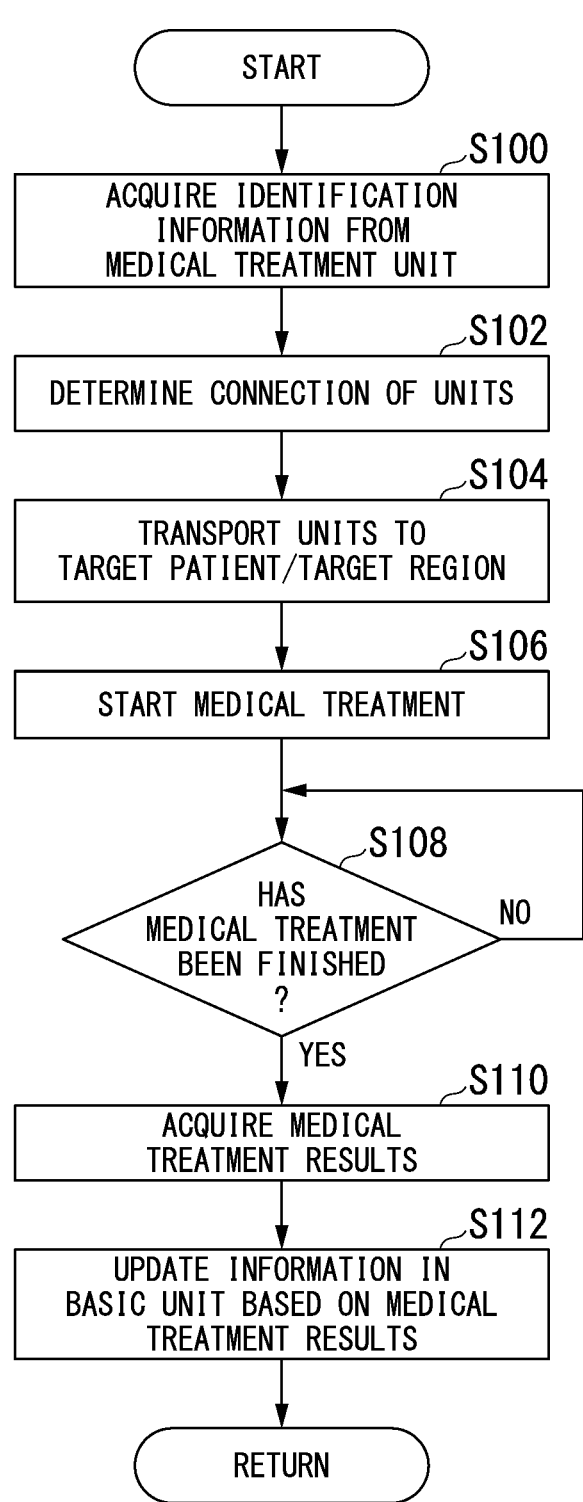
FIG. 3 is a flowchart showing the flow of the overall processing of a mobile diagnosis system of the first embodiment.

Hereinafter, the flow of the overall processing of the mobile diagnosis system 1 will be described focusing mainly on the processing of the processing circuitry 120 of the transport management device 100 with reference to a flowchart. FIG. 3 is a flowchart showing a flow of the overall processing of the mobile diagnosis system 1 in the first embodiment. The processing of this flowchart may be executed when at least the basic unit U0 is loaded on the trailer truck T.

First, the acquisition function 121 acquires identification information unique to each piece of medical equipment (hereinafter referred to as a medical equipment ID) from the medical equipment 200 stored in each of the medical treatment units Ux loaded on the trailer truck T via the communication interface 111 (step S100).

The medical equipment ID may include information for identifying the type of medical equipment 200, such as whether it is an X-ray CT device, an MRI device, or a sound wave image diagnosis device. Alternatively, some medical equipment 200 of the same type has different uses. In this case, the medical equipment ID may include information by which its use can be identified.

Specifically, even for the medical equipment 200 of the same type such as medical equipment 200-A used for medical treatment of the circulatory system, medical equipment 200-B used for medical treatment of the digestive system, and medical equipment 200-C used for medical treatment of the head, their uses (parts to be subjected to medical treatment) may be different. In this case, a medical equipment ID of the medical equipment 200-A may include information by which it can be identified that a target for medical treatment is the circulatory system, a medical equipment ID of the medical equipment 200-B may include information by which it can be identified that a target for medical treatment is the digestive system, and a medical equipment ID of the medical equipment 200-C may include information by which it can be identified that a target for medical treatment is the head.

Next, the determination function 122 determines connection of the units based on the medical equipment ID acquired by the acquisition function 121 (step S102).

For example, the determination function 122 determines whether or not a combination of the medical treatment units Ux loaded on the trailer truck T is a combination of units suitable for target patients and target regions to which the units are to be transported. "Suitable for target patients and target regions" means that desired medical services can be provided to the target patients, and desired medical services can be provided in the target regions.

Figure 4:
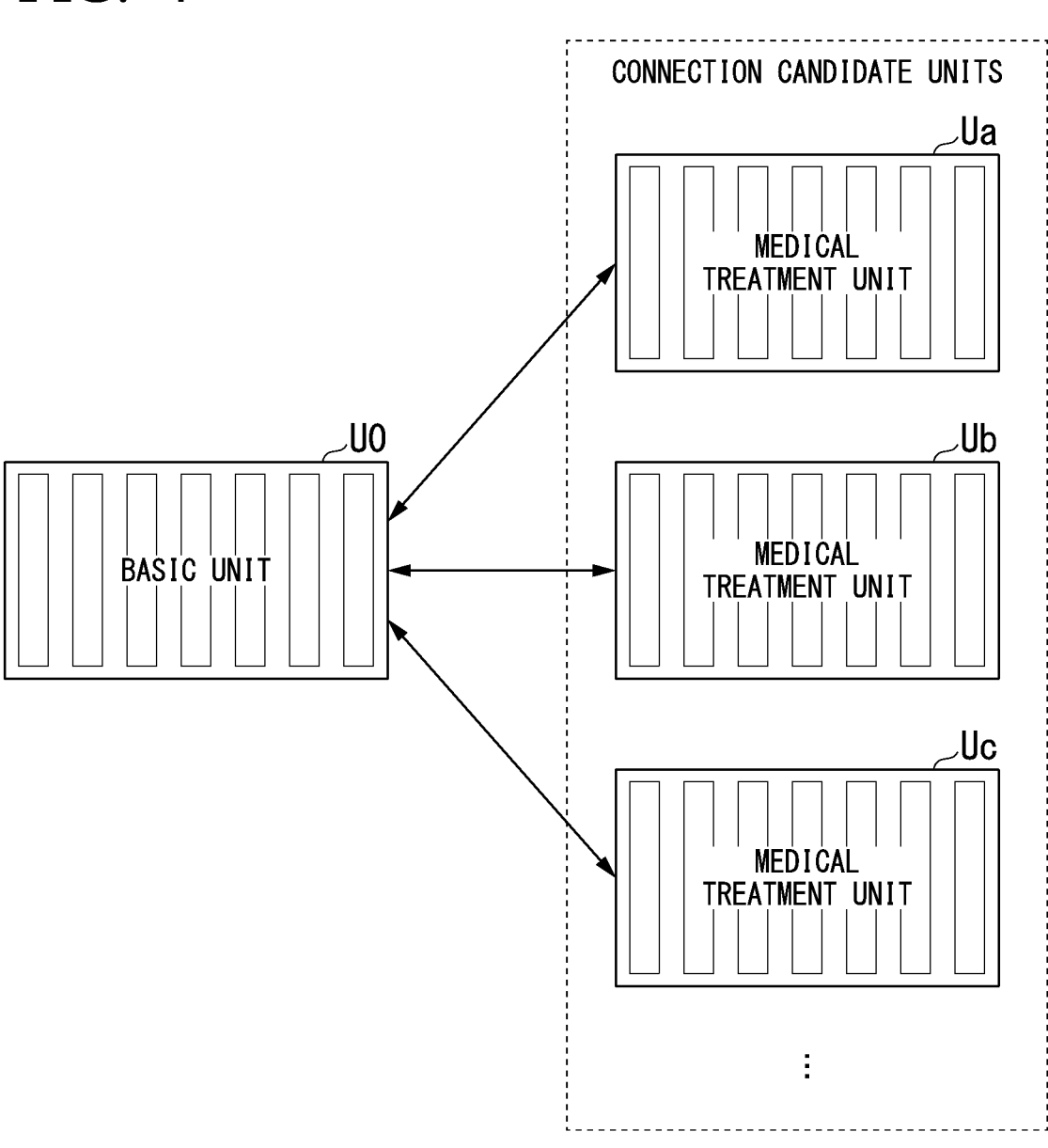
FIG. 4 is a diagram illustrating a method of determining a combination of units.

FIG. 4 is a diagram illustrating a method of determining a combination of units. For example, it is assumed that the units that can be loaded on the trailer truck T include a basic unit U0, a medical treatment unit Ua that stores the medical equipment 200-A for a "circulatory system", a medical treatment unit Ub that stores the medical equipment 200-B for a "digestive system", and a medical treatment unit Uc that stores the medical equipment 200-C for a "head".

For example, when a certain target patient suffers from heart disease, the target patient is required to medical treatment for the heart. In such a case, a combination of units suitable for the target patient suffering from heart disease is a combination of the basic unit U0 and the medical treatment unit Ua that stores the medical equipment 200-A for a "circulatory system".

Consequently, the determination function 122 determines whether the medical treatment unit Ua that stores the medical equipment 200-A for a "circulatory system" is included in the medical treatment units Ux loaded on the trailer truck T with reference to the medical equipment IDs acquired from the medical equipment 200 of the medical treatment units Ux by the acquisition function 121. When there is no medical treatment unit Ua, the determination function 122 determines that the combination of the medical treatment units Ux loaded on the trailer truck T is not a combination of units suitable for the target patient. On the other hand, when there is the medical treatment unit Ua, the determination function 122 determines that the combination of the medical treatment units Ux loaded on the trailer truck T is a combination of units suitable for the target patient.

When it is determined that the combination of the medical treatment units Ux loaded on the trailer truck T is not a combination of units suitable for the target patient or a target region, the output control function 123 may output an alert or the like via the output interface 113.

A combination of units suitable for a target patient or a target region may be designated by, for example, an input of a doctor or the like to the input interface 112, or may be acquired via the communication interface 111 from a computer that can be used by a doctor or the like. In addition, the determination function 122 may automatically determine a combination of units suitable for a target patient or a target region from electronic medical records stored in the memory 114 by using machine learning or the like.

When it is determined that the combination of the medical treatment units Ux loaded on trailer truck T is a combination of units suitable for the target patient or the target region, the units are transported to the target patient or the target region by the trailer truck T (step S104).

Next, medical treatment of the target patient or people in the target region is started using the medical equipment 200 stored in the medical treatment unit Ux (step S106).

The determination function 122 may determine diagnosis conditions for each medical equipment 200 based on the electronic medical records stored in the memory 114 when medical treatment is started. For example, when the medical equipment 200 is an X-ray CT device or an MRI device, the determination function 122 may determine imaging conditions for the X-ray CT device or the MRI device. The diagnosis conditions (imaging conditions and the like) determined by the determination function 122 are transmitted to the medical equipment 200 via the communication interface 111. In response to this, the medical equipment 200 operates in accordance with the diagnosis conditions determined by the determination function 122.

Next, the acquisition function 121 waits until the medical treatment for the target patient or the people in the target region is finished (step S108), and when the medical treatment is finished, medical treatment results are acquired from the medical equipment 200 via the communication interface 111 (step S110). The medical treatment results may include various medical images such as MR images and CT images.

Next, the acquisition function 121 updates the electronic medical records stored in the memory 114 using the medical treatment results (step S112). Thus, the processing of this flowchart is finished. Hereinafter, when a target patient or a target region is newly designated, the units loaded on the trailer truck T are rearranged into those suitable for the new target patient or target region, and transported to the new target patient and target region.

According to the first embodiment described above, the transport management device 100 confirms whether a combination of units suitable for the target patient and the target region is loaded on the trailer truck T, and then the units are transported. Thus, even people with various problems, such as an uneven distribution of doctors, aging of doctors, the lack of social infrastructure, can receive appropriate medical services when they need them.

Second Embodiment

Hereinafter, a second embodiment will be described. The second embodiment is different from the above-described first embodiment in that, when a plurality of units are scattered in regions different from a target region, a transport plan for suitably transporting the units scattered in the regions to the target region is determined. Hereinafter, a description will be given focusing on differences from the first embodiment, and points in common with the first embodiment will not be described. In the description of the second embodiment, the same portions as those in the first embodiment will be denoted by the same reference numerals and signs.

Figure 5:
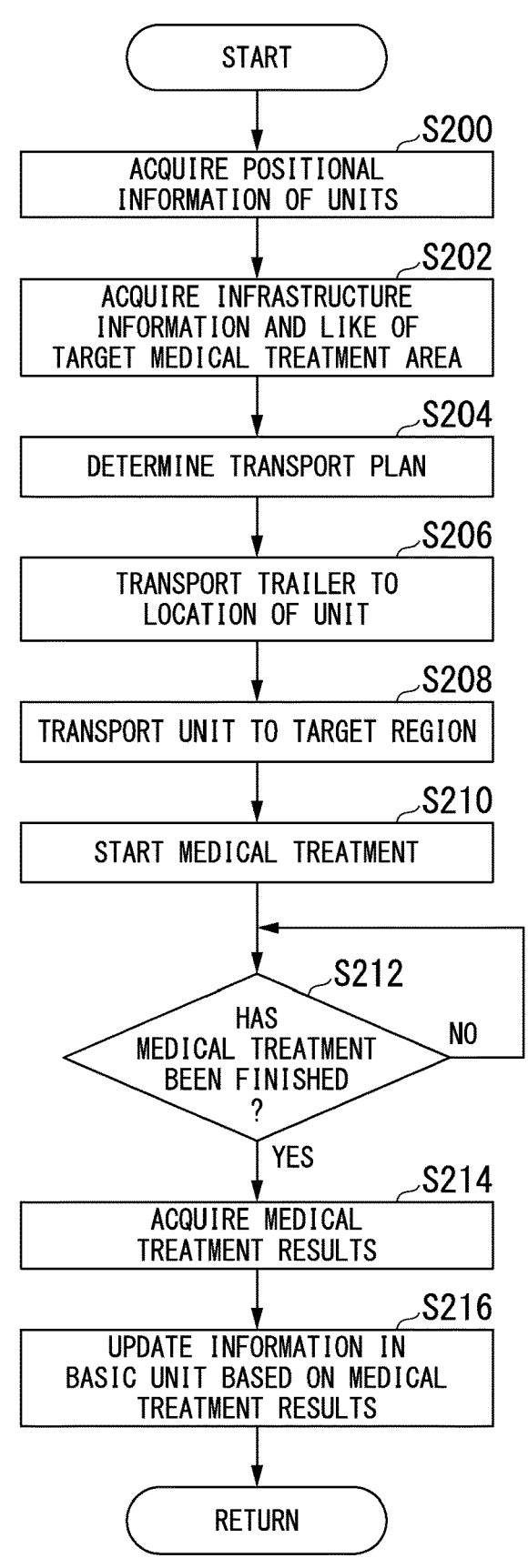
FIG. 5 is a flowchart showing the flow of the overall processing of a mobile diagnosis system of the second embodiment.

FIG. 5 is a flowchart showing the flow of an overall processing of a mobile diagnosis system 1 in the second embodiment. The processing of this flowchart may be executed when a target region, which is a transport destination of units scattered in various parts, is designated. Further, in the second embodiment, the transport management device 100 does not necessarily need to be stored in a container, and may be, for example, one of servers on a communication network NW. When the transport management device 100 is not stored in the container, the basic unit U0 may store a computer with functions equivalent to those of the transport management device 100.

First, an acquisition function 121 in the second embodiment acquires positional information of the units scattered in various parts (step S200).

Figure 6:
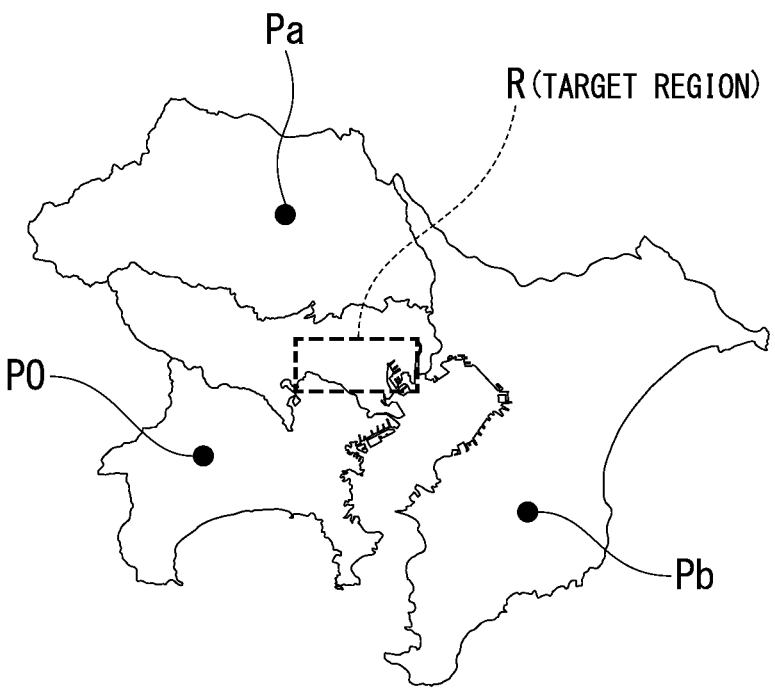
FIG. 6 is a diagram illustrating a state where units are scattered in various parts.

FIG. 6 is a diagram illustrating a state where units are scattered in various parts. For example, it is assumed that a basic unit U0 is located at a certain point P0, a medical treatment unit Ua that stores the medical equipment 200-A for a "circulatory system" is located at a certain point Pa, and a medical treatment unit Ub that stores the medical equipment 200-B for a "digestive system" is located at a certain point Pb. In such a case, the acquisition function 121 accesses the units located at P0, Pa, and Pb via a communication interface 111 and acquires positional information of the units (for example, global positioning system (GPS) coordinates and the like).

Next, the acquisition function 121 determines an area including at least a target region and a transport route from a point where the units are scattered to the target region, and acquires geographic information and/or infrastructure information of the area (step S202). The geographic information may include, for example, information on the state of mountains and rivers in the land, and information on the altitude of the land. The infrastructure information may include, for example, information on road traffic networks, power networks, water and sewerage networks, mobile communication networks, and the like.

The acquisition function 121 may further acquire an infection distribution in the area including the target region and the transport route. In such a case, it is assumed that the infection of disease is spreading in a certain region, and medical treatment for people infected with the disease is requested. In such cases, the region where the infection of the disease has spread becomes a target region. In such a case, the acquisition function 121 may acquire the number of infected people and their distribution around the target region.

Next, the determination function 122 in the second embodiment determines a transport plan for transporting the units scattered in various parts to the target region based on the geographic information and/or the infrastructure information (step S204).

At this time, the determination function 122 may determine a transport plan based on an infection distribution of disease spreading in the area including the target region and the transport route, in addition to or instead of the geographic information and/or the infrastructure information.

Figure 7:
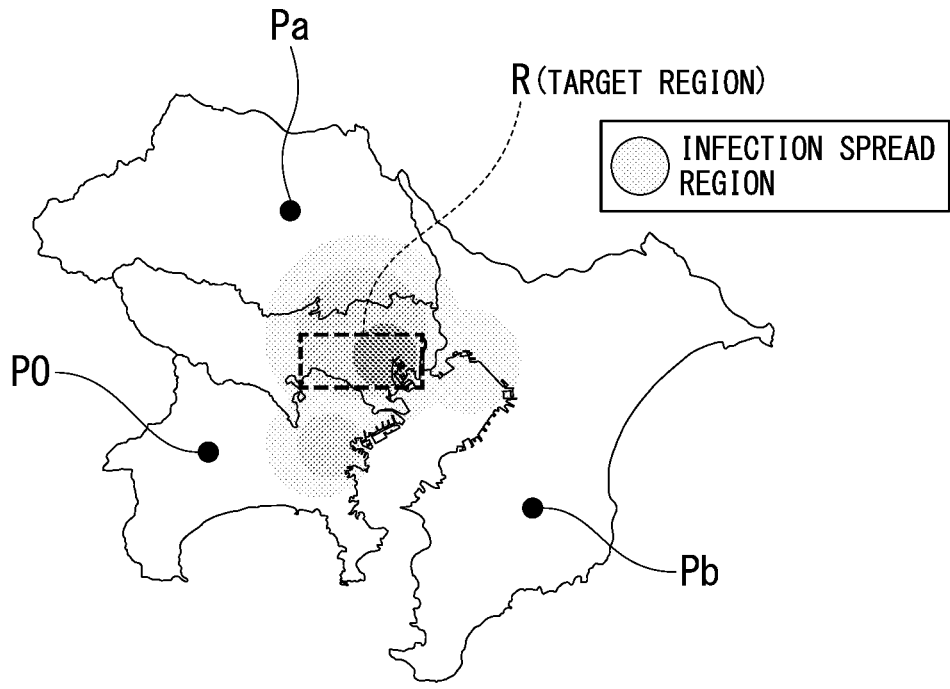
FIG. 7 is a diagram illustrating an example in which a transport plan is determined based on an infection distribution of a disease.

FIG. 7 is a diagram illustrating an example in which a transport plan is determined based on an infection distribution of disease. For example, when there are units at both a point where the infection of disease is not spreading (a point where the number of infected people is small) and a point where the infection of disease is spreading (a point where the number of infected people is large), the determination function 122 may determine a transport plan for transporting the unit located at the point where the infection of disease is not spreading (the point where the number of infected people is small) to the target region with preference over the unit located at the point where the infection of disease is spreading (the point where the number of infected people is large). In the example illustrated in the drawing, P0, Pa, and Pb are outside the infection spread region, and thus a transport plan for transporting all of the units located at P0, Pa, and Pb to a target region R is determined.

Description will return to the flowchart of FIG. 5. Next, the trailer truck T is transported to the location of the unit in accordance with the transport plan, and the trailer truck T picks up the units at various parts (step S206).

Next, the units picked up by the trailer truck T are transported to the target region (step S208).

Next, medical treatment for people in the target region is started using the medical equipment 200 of the medical treatment unit Ux transported to the target region (step S210).

Next, the acquisition function 121 waits until the medical treatment for the people in the target region is finished (step S212), and when the medical treatment is finished, medical treatment results are acquired from the medical equipment 200 via the communication interface 111 (step S214).

Next, the acquisition function 121 updates the electronic medical records stored in the memory 114 using the medical treatment results (step S216). Thereby, the processing of this flowchart is finished.

According to the second embodiment described above, when a plurality of units are scattered in a second region different from a target region, the transport management device 100 determines a transport plan for transporting the units located at various parts to the target region. Thereby, it is possible to efficiently use limited medical resources.

Although some embodiments have been described, these embodiments have been presented as examples and are not intended to limit the scope of the invention. These embodiments can be embodied in various other forms, and various omissions, substitutions, and modifications can be made without departing from the gist of the invention. These embodiments and their modifications are included in the scope and spirit of the invention, as well as the scope of the invention described in the claims and equivalents thereof.

What is claimed is:

1. A mobile diagnosis system, comprising:
a plurality of containers configured to store medical equipment and configured to be combined with each other;
a mobile body configured for a combination of the containers suitable for a person or a region requiring a medical service among the plurality of containers to be loaded thereon, and configured to transport the containers to the person or the region; and

a transport management device configured to manage transportation of the containers,
wherein each of the plurality of containers is loaded with the medical equipment having different types from each other, and
wherein the transport management device includes processing circuitry configured to
when the plurality of containers are scattered in a second region different from a target region, which is the region requiring the medical service, acquire positional information of each of the plurality of containers;
determine an area including the target region and a route from the second region to the target region; and
determine a transport plan for the plurality of containers based on at least one of geographic information and infrastructure information of the area.

2. The mobile diagnosis system according to claim 1, wherein the processing circuitry is further configured to determine whether the combination of the containers loaded on the mobile body is a combination of the containers suitable for the person or the region.

3. The mobile diagnosis system according to claim 2, wherein the transport management device is stored in any one container loaded on the mobile body, and the combination of the containers suitable for the person or the region includes at least the container in which the transport management device is stored.

4. The mobile diagnosis system according to claim 2, wherein the processing circuitry is further configured for the plurality of containers to be transported to the person or the region by the mobile body, and when the medical service is provided using the medical equipment stored in each of the plurality of containers transported, medical treatment results are acquired from each piece of medical equipment.

5. The mobile diagnosis system according to claim 1, wherein the processing circuitry is further configured to determine the transport plan based on an infection distribution of a disease spreading in the area.

6. A transportation management device, comprising:
processing circuitry configured to manage transportation of a plurality of containers, storing medical equipment and capable of being combined with each other, to a person or a region requiring a medical service such that a combination of the containers suitable for the person or the region among the plurality of containers is loaded on a mobile body,
wherein each of the plurality of containers is loaded with the medical equipment having different types from each other, and
wherein the processing circuitry is further configured to
when the plurality of containers are scattered in a second region different from a target region, which is the region requiring the medical service, acquire positional information of each of the plurality of containers;
determine an area including the target region and a route from the second region to the target region; and
determine a transport plan for the plurality of containers based on at least one of geographic information and infrastructure information of the area.

7. The mobile diagnosis system according to claim 1, wherein the geographic information includes at least one of information on a state of mountains and rivers in the area, and an altitude of the area.

8. The mobile diagnosis system according to claim 1, wherein the infrastructure information includes at least one of information on road traffic networks, power networks, water and sewerage networks, and mobile communication networks.

9. The mobile diagnosis system according to claim 1, wherein the processing circuitry is further configured to:

access each of the plurality of containers via a communication interface; and acquire global positioning system coordinates of each of the plurality of containers as the positional information.

10. The mobile diagnosis system according to claim 1, wherein the processing circuitry is further configured to:

transport the mobile body to a location of each of the plurality of containers in accordance with the transport plan; and cause the mobile body to pick up the plurality of containers.

\* \* \* \* \*